United States Patent [19]

Koch

[11] Patent Number: 4,961,436

[45] Date of Patent: Oct. 9, 1990

[54] CONTRACEPTIVE CERVICAL CAP

[75] Inventor: James P. Koch, Brookline, Mass.

[73] Assignee: Brigham and Women's Hospital, Boston, Mass.

[21] Appl. No.: 338,517

[22] Filed: Apr. 12, 1989

Related U.S. Application Data

[63] Continuation of Ser. No. 74,992, Jul. 17, 1987, abandoned.

[51] Int. Cl.⁵ .............................................. A61F 5/46
[52] U.S. Cl. .................................... 128/837; 128/834; 128/841
[58] Field of Search ................ 128/830, 832, 834, 835, 128/836, 837, 841

[56] References Cited

U.S. PATENT DOCUMENTS

| 92,417 | 7/1869 | Angell | 128/128 |
|---|---|---|---|
| 1,103,114 | 7/1914 | Warren | 128/127 |
| 2,818,856 | 1/1958 | Kohl | 128/838 |
| 2,836,177 | 5/1958 | Sells | 128/127 |
| 3,036,570 | 5/1962 | Milgrom et al. | 128/127 |
| 3,404,682 | 10/1968 | Waldron | 128/127 |
| 3,952,737 | 4/1976 | Lipfert et al. | 128/127 |
| 4,007,249 | 2/1977 | Erb | 264/222 |
| 4,320,751 | 3/1982 | Loeb | 128/127 |
| 4,322,463 | 3/1982 | Goepp et al. | 428/138 |
| 4,363,318 | 12/1982 | Goepp et al. | 128/130 |

FOREIGN PATENT DOCUMENTS

| 385401 | 12/1921 | Fed. Rep. of Germany | 128/127 |
|---|---|---|---|
| 414541 | 7/1923 | Fed. Rep. of Germany | |
| 475496 | 4/1929 | Fed. Rep. of Germany | |
| 557914 | 8/1932 | Fed. Rep. of Germany | |
| 734071 | 10/1932 | France | |
| 198122 | 11/1964 | Sweden | 128/127 |
| 243186 | 11/1925 | United Kingdom | |

Primary Examiner—Robert A. Hafer
Assistant Examiner—Kevin G. Rooney
Attorney, Agent, or Firm—Saidman, Sterne, Kessler & Goldstein

[57] ABSTRACT

A cervical cap for covering a portion of the cervix uteri in order to prevent migration of sperm from the vagina into the cervical canal to thereby prevent conception. The cervical cap has an open end portion, a dome-shaped portion, preferably sealed, disposed opposite the open end portion, and a ridged section designed to grip the cervix to secure the cap. In the preferred embodiments, the ridged section has a plurality of substantially parallel ring-shaped ridges formed on the interior surface of the cap. In an alternate embodiment, a helical-shaped ridge is formed on the interior surface of the cap and extends from the rim to the dome portion, progressively narrowing in width.

19 Claims, 4 Drawing Sheets

CONTRACEPTIVE CERVICAL CAP

This application is a continuation of application Ser. No. 074,992, filed July 17, 1987 abandoned.

BACKGROUND OF THE INVENTION

1. Field of the Invention

The present invention relates to an apparatus for covering a portion of the cervix uteri to prevent the migration of sperm from the vagina into the cervical canal and more particularly to a cervical cap having a ridged section adapted to grip the cervix, thus preventing dislodgement (or displacement) of the cap (or thus increasing cap stability).

2. Description of the Related Art

Cervical caps designed to cover a portion of the cervix uteri in order to prevent the migration of sperm from the vagina into the cervical canal and thereby prevent conception are known in the art. However, these known caps suffer several drawbacks and deficiencies.

Known cervical caps create medical problems for the user, such as abnormal cramps, abnormal bleeding, abnormal discharge from the uterus, and mucosal erythema. Furthermore, known caps, due to their size and shape, cause discomfort for both the user as well as for the partner.

Another problem encountered with prior cervical caps is the frequency with which they become dislodged from the cervix. These caps rotate on the cervix or slide from the surface of the cervix when the rim is gently pushed. The result of such dislodgement is not only increased discomfort but the defeat of the very purpose behind using the cervical cap because dislodgement allows sperm to migrate into the cervical canal which can result in conception.

Therefore, attempts have been made to design a reliable cervical cap that securely fits around a portion of the cervix while still avoiding the aforementioned medical problems and the associated inconveniences and discomfort. Such attempts have taken a variety of forms. For example, some caps have been designed with a spring mechanism within the wall; some caps have been provided with adhesive to adhere the cap to the cervix (see, for example, U.S. Pat. No. 3,952,737); and some have been provided with projections on the inner surface. However, these caps have not only failed to solve the problems discussed above, but have created additional problems. For example, U.S. Pat. No. 3,952,737 discloses a cervical cap which is held to the cervix by an O-ring, notches, an internal bead and an inner sealing ring. This device, however, in attempting to solve the dislodgement problem, has resulted in a cap that is both expensive to manufacture due to its complexity and is difficult to use because it is inserted with an applicator and the 0-ring must be maneuvered from the bottom position to the top position after the cap has been placed on the cervix.

A need therefore exists for a cervical cap that is comfortable and reliable as a contraceptive. Furthermore, a need exists for such a comfortable and reliable cap that is simple to use, is not prohibitively expensive, and does not adversely affect the health of the user.

SUMMARY OF THE INVENTION

The present invention overcomes the aforementioned problems and deficiencies in the art. The present invention provides an apparatus for covering a portion of the cervix uteri which comprises a cap having inner and outer surfaces and an open end portion. The inner surface has a ridged section which is adjacent to the open end portion. The ridged section is adapted to grip the cervix when the cap is placed over a portion of the cervix. The ridged section has first and second ridge portions projecting inwardly from the inner surface of the cap. The distance between the open end portion and the first ridge portion is less than the distance between the open end portion and the second ridge portion.

More particularly, in one embodiment, the first and second ridge portions are substantially ring shaped and are disposed in substantially parallel relationship to each other. Preferably, the first ridge portion is formed at a rim of the cap. The inside diameter of the ridged section at the first ridge portion is substantially equal to the inside diameter of the ridged section at the second ridge portion. The cap may further include a third ring-shaped ridge disposed between the first and second ridges and in substantially parallel relationship to the first and second ridges. The cap preferably terminates in a rounded edge region at the open end portion.

The cap may have a reduced diameter rim section relative to the diameter of the ridged section. Alternatively, the cap may have an enlarged diameter rim section relative to the diameter of the ridged section. A region of the cap adjacent to the ridged section may be tapered so that the inside diameter at that region is less than the inside diameter at the ridged section. The ridged section of the cap may also be tapered so that the distance between the inner and outer surfaces is greater at the first ridge portion than at the second ridge portion.

In an alternate embodiment of the present invention, the first and second ridge portions of the cap are connected to form a continuous helical shaped ridge wherein the inside diameter of the cap at the ridged section remains substanstantially constant or progressively decreases away from the open end portion. Preferably, the first ridge portion is formed at the rim of the cap. The cap may terminate at a rounded edge region at the open end portion. Alternatively, a flange-like projection is formed at the rim of the cap which extends outwardly from the open end portion. The ridged section of the cap may be tapered such that the distance between the inner and outer surfaces is greater at the first ridge portion than at the second ridge portion.

The cap may further comprise a dome-shaped portion which is disposed opposite the open end portion and is preferably of substantially uniform thickness. The dome-shaped portion is preferably sealed and has an inside diameter which progressively increases towards the ridged section.

BRIEF DESCRIPTION OF THE DRAWINGS

Various objects, features, and attendant advantages of the present invention will be more fully appreciated as the same becomes better understood from the following detailed description of the present invention when considered in connection with the accompanying drawings in which:.

DESCRIPTION OF THE PREFERRED EMBODIMENTS

Figure 1:
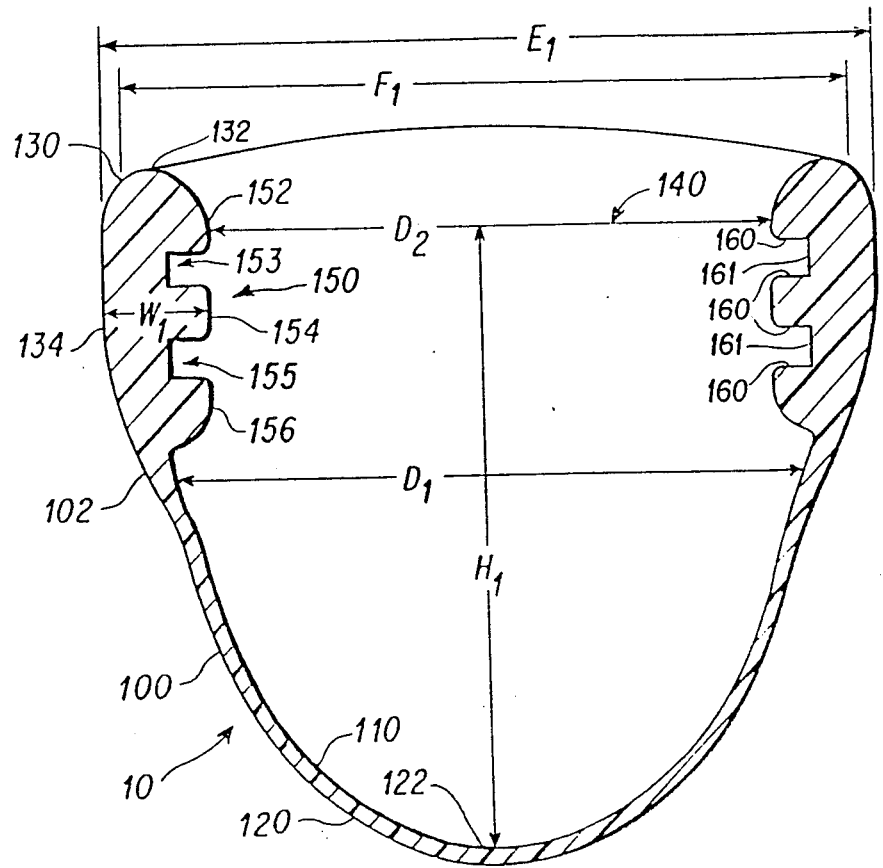
FIG. 1 is a cross-sectional view illustrating a preferred embodiment of the cervical cap of the present invention.

In the drawings, the several embodiments of the invention are shown in longitudinal cross-section. That is, the cap is essentially dome- or bell-shaped; the axis of rotation of the drawing lies in the plane of the drawing. Like reference numerals prefixed with the figure number represent corresponding parts in the several views. Thus, the cervical cap of the present invention is indicated generally by reference numeral 10 in FIG. 1, by 20 in FIG. 2, by 30 in FIG. 3, and by 40 in FIG. 4. The cervical cap, made preferably of natural or resilient synthetic rubber, is inserted to cover the vaginal portion of the cervix uteri and is designed to be impenetrable in normal use so as to prevent sperm from migrating into the cervical canal, thereby preventing conception.

In the embodiment shown in FIG. 1, the cervical cap 10 has an outer surface 100 and an inner surface 110. The cervical cap 10 includes a dome portion 120, a rim 130, and an opening 140. The opening 140, defined by the rim 130, is disposed opposite the dome portion 120 and is of sufficient size to fit over the vaginal portion of the cervix uteri. The rim 130 has a rounded edge top portion 132 located at opening 140 where the cap 10 terminates.

The dome portion 120 is substantially semicircular in shape, and preferably has a uniform thickness measuring about 0.8 mm to about 1 mm, depending on the material used to construct the dome. The dome portion 120 is preferably sealed to effectively prevent the migration of sperm into the cervical canal. The dome portion 120 is tapered so that the inside diameter of the cap 10 progressively decreases toward a tip 122 of the dome. Preferably and advantageously, and depending on the size of the cervix, which varies widely among women and may change in a given woman as a result of childbirth, the inside diameter D1 at the widest section of dome portion 120 of the cap 10 may vary from about 22 mm to about 34mm. The height H of the cap 10, measured from opening 140 to tip 122, may vary from about 25 mm to about 40 mm. The inside diameter D2 of the rim 130 may vary from about 19 mm to about 32 mm. Therefore, a cervical cap is provided which advantageously combines small size, comfort, and reliability.

The rim 130 has a circumferential ridge section 150 between top portion 132 and dome portion 120. Section 150 contains a plurality of blunt edged ridges on its inner surface. The ridged section 150 effectively functions to secure cap 10 to the cervix by firmly but gently pressing against the surface of the cervix uteri. This uniquely shaped ridged section 150 helps to provide an airtight and substantially fluid-tight fit and prevents dislodgement of the cap which would cause an increase in the chance of conception. Preferably, a gel, cream, or foam-type spermicide is provided in the space defined by the dome portion 120 to provide further contraceptive protection.

FIG. 1 illustrates the embodiment of the cervical cap 10 of the present invention having a ridged section 150 which comprises three ring-shaped ridges 152, 154, and 156. The three ring-shaped ridges 152, 154, and 156 are preferably disposed in parallel relationship to each other with the outer ridge 152 forming a part of the rim 130 of the cap 10. A space or recess 153 is defined by a pair of substantially parallel walls 160 and a third wall 161 substantially perpendicular to the pair of walls 160 and is located between the outer ridge 152 and the middle ridge 154, and a space or recess 155, similar to recess 153, is defined between the middle ridge 154 and inner ridge 156. The three ridges 152, 154, and 156 are preferably of equal width or thickness W so that the distance between the inner surface 110 and the outer surface 100 at each of the ridges 152, 154, and 156 is approximately equal. In the preferred embodiment, W1 measures about 4 mm. Preferably, the depth of each of the recesses 153 and 155 is about 1.5 mm. The outside diameter E1 at the rim section 130 preferably measures about 28–40.

Obviously, a range of appropriate cap sizes will be provided. Values for the cap diameters and ridge spaces will be selected to effectively secure the cap 10 to the cervix of the particular wearer.

Finally, cap 10 as illustrated in FIG. 1 tapers slightly inwardly from the top portion 130 along section 132 adjacent the cap opening 140.

Figure 2:
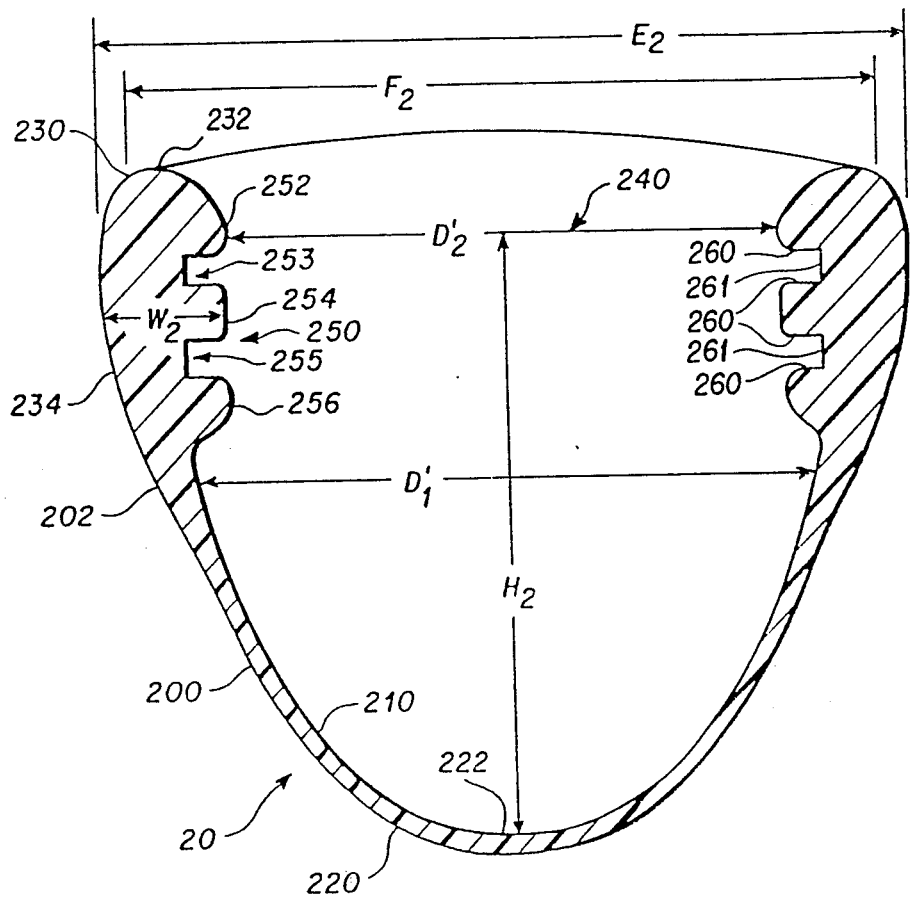
FIG. 2 is a cross-sectional view of an alternate embodiment of the cervical cap of the present invention.

The version of the cervical cap shown in FIG. 2 differs from that of FIG. 1 primarily with respect to the shapes of the respective ridge sections. In the embodiment of FIG. 2, the ridge region 250 is thicker than the corresponding ridge region 150 in FIG. 1. Thus W2, the thickness of region 250, is greater than W1. The portion 202 joining rim region 234 with dome region 220 has a longer taper than the corresponding portion 102 in FIG. 1. Diameter E2, the outer diameter of rim 230 measures about 32–44 mm. Preferably, the thickness or width W2 of ridge region 250 decreases from the outer ridge 252 to the inner ridge 256, as shown in FIG. 2, to provide the desired combination of rigidity and flexibility.

Figure 3:
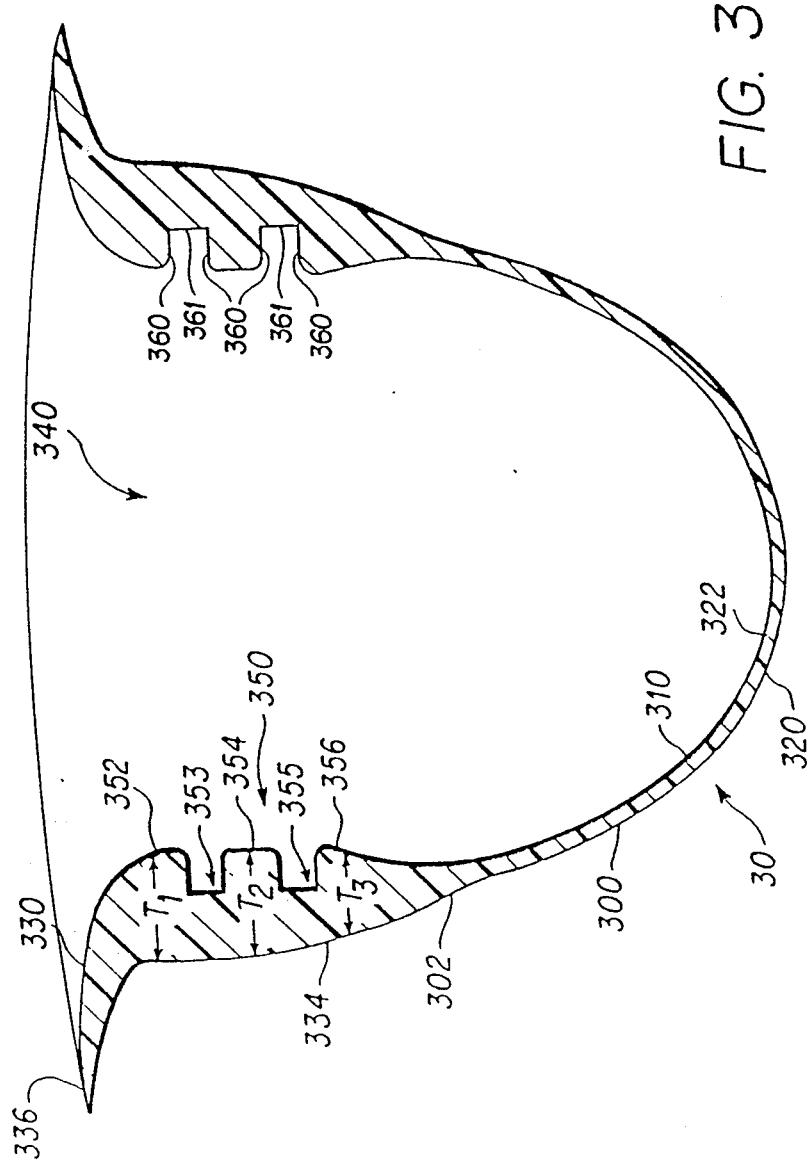
FIG. 3 is a cross-sectional view of another alternate embodiment of the cervical cap of the present invention.

FIG. 3 illustrates yet another alternate embodiment of the cervical cap having parallel ring-shaped ridges to grip the cervix. The cap 30 has a ridged section 350 which includes an outer ridge 352, an middle ridge 354, and an inner ridge 356. A recess 353 is defined between outer ridge 352 and middle ridge 354, and a recess 355 is defined between middle ridge 354 and inner ridge 356. The ridged section 350 is tapered so that the distance between the inner surface 310 and outer surface 300 decreases from outer ridge 352 to inner ridge 356, whereby the width or thickness of ridges 352, 354, and 356 vary. In one specific example, the thickness T1 between the outer and inner surfaces 300 and 310 at the outer ridge 352 is preferably about 5 mm, the thickness T2 between the outer and inner surfaces 300 and 310 at the middle ridge 354 is preferably about 4 mm, and the thickness T3 between the outer and inner surface 300 and 310 at the inner ridge 356 is preferably about 3 mm. Obviously, other dimensional relationships which achieve the same function and result are possible.

The cervical cap embodiment in FIG. 3 is shown with a flange 336 extending outwardly from rim 330 away from opening 340. While the cap can be constructed in this way, the preferred versions do not include the flange 336. In the more preferred versions, the rim is rounded, as the embodiments shown in FIGS. 1, 2, and 4.

Figure 4:
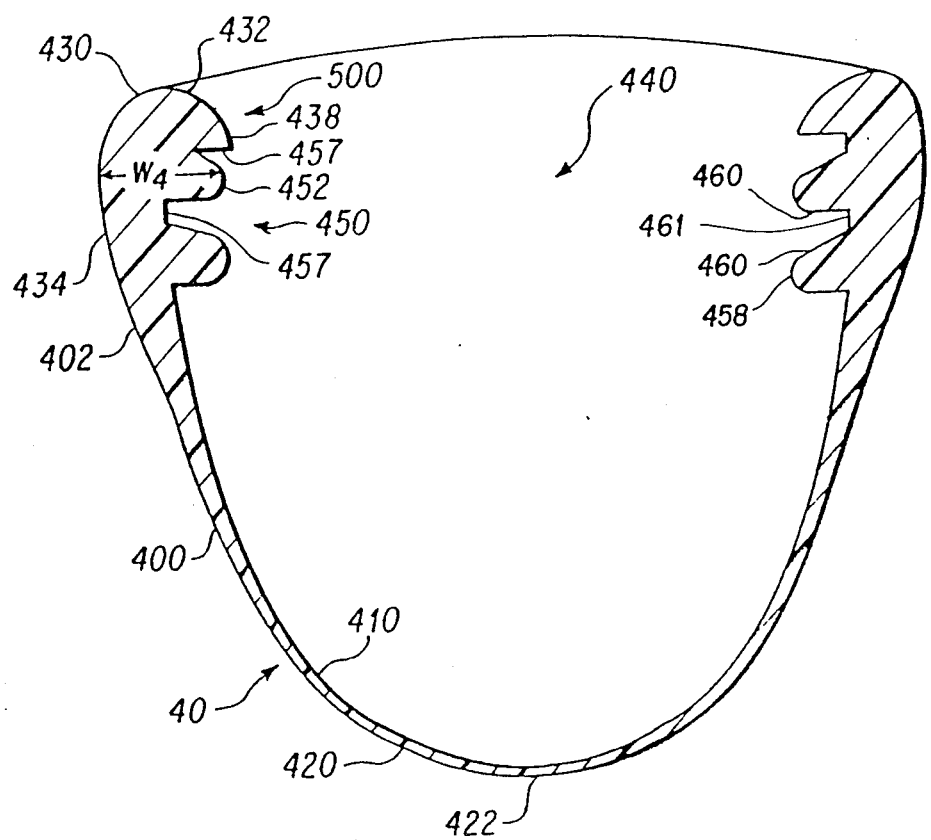
FIG. 4 is a cross-sectional view of still another alternate embodiment of the cervical cap.

FIG. 4 illustrates another alternate embodiment of the cervical cap of the present invention. The cap 40 has a ridged section 450 which comprises a helical shaped ridge 452 formed on inner surface 410. The helical shaped ridge 452 enables the cap 40 to be screwed onto the exterior surface of the cervix to provide a secure fit.

In the embodiment shown in FIG. 4, the helical-shaped ridge 452 extends from an inner portion 438 of rim 430. Rim 430 terminates preferably in a rounded edge region 432. Helical ridge 452 terminates at its inner end 458, adjacent portion 402 which joins wall region 434 and dome region 420. The width or thickness W4 of ridge region 450 between the inner surface 410 and outer surface 400 along the helical-shaped ridge 452 preferably remains substantially constant or continuously decreases away from opening 440 until the inner portion 458 is flush with inner surface 440. A space or recess 457 is defined between the adjacent rows of helical ridge 452 by walls 160, 161 as described above. The inside diameter of the cap 10 at spaces 457 is from about 18 mm to about 35 mm.

When the cervical cap of the present invention is inserted, preferably digitally or with a suitable insertion tool, over the vaginal portion of the cervix uteri, the substantially parallel walls 160 of the ridge section remain substantially fixed relative to each other and function to grip that portion of the cervix both firmly and gently to effectively prevent the dislodgement of the cap. There is no need for additional securing features, as the unique dimensions of the cap, including the shape and size of the dome, as well as the unique location and formation of the ridges secure the cap in position. Both the ring-shaped ridges and the helical-shaped ridge advantageously provide for easy insertion and a secure fit.

Obviously, numerous modifications and variations of the present invention are possible in light of the above teachings. It is therefore to be understood that within the scope of the appended claims, the invention may be practiced otherwise than as specifically described herein.

What is claimed is:

1. A cervical cap for covering a portion of the cervix uteri comprising:
   a dome portion, a rim portion, and an open end portion made of a flexible material;
   a ridge section, disposed between said dome portion and said rim portion, extending circumferentially around the inner surface of said cap adjacent to said open end portion;
   a recess formed in said ridged section by a pair of first and second substantially parallel walls and a third wall substantially perpendicular to said first and second walls; and
   first and second ridge portions defined by said recess along said inner surface of said cap, said first and second ridge portions having a blunt inner edge;
   whereby said ridged section is adapted to grip the outer surface of the cervix and said first and second walls are adapted to remain substantially fixed and substantially parallel to form a substantially fluid-tight fit with said cervix while said cap is placed over a portion of the cervix.

2. A cervical cap as recited in claim 1, wherein said first and second ridge portions are substantially ring shaped and are disposed in substantially parallel relationship to each other.

3. A cervical cap as recited in claim 2, wherein said ridged section has a wall thickness at said first ridge portion which is substantially equal to the ridged section wall thickness at said second ridge portion.

4. A cervical cap as recited in claim 3, wherein said rim portion includes a rounded edge region at said open end portion.

5. A cervical cap as recited in claim 3, further comprising a tapered region between and connecting said ridged section and said dome portion.

6. A cervical cap as recited in claim 1, wherein said first and second ridge portions are integral to form a continuous helical shaped ridge.

7. A cervical cap as recited in claim 6, wherein the inside diameter of said cap at said ridged section progressively decreases away from said open end portion.

8. A cervical cap as recited in claim 7, wherein said first ridge portion is formed at a rim of said cap.

9. A cervical cap as recited in claim 8, wherein said cap terminates in a rounded-edge region at said open end portion.

10. A cervical cap for covering a portion of the cervix uteri comprising:
    a rim portion, an open end portion, a ridged section, and a dome-shaped portion made of a flexible resilient material;
    said dome-shaped portion being disposed opposite said open end portion;
    said ridged section having inner and outer surfaces;
    first and second ring-shaped ridge portions defined by a recess formed by substantially parallel walls along said inner surface, said first and second ring-shaped ridge portions having a blunt inner edge;
    said ridged section being located adjacent said open end portion and being adapted to grip the cervix, and
    said substantially parallel walls being adapted to remain substantially fixed and substantially parallel to form a substantially fluid tight fit while said cap is placed over a portion of the cervix.

11. A cervical cap as recited in claim 10, wherein said dome-shaped portion is sealed.

12. A cervical cap as recited in claim 11, further comprising a third ring-shaped ridge disposed substantially between said first and second ridges, and in substantially parallel relationship to said first and second ridges.

13. A cervical cap as recited in claim 12, wherein the inside diameter of said dome-shaped portion progressively increases towards said ridged section.

14. A cervical cap for covering a portion of the cervix uteri comprising: a rim portion; and open end portion; a dome-shaped portion disposed opposite said open end portion; and a ridged section located adjacent said open end portion and adapted to grip the cervix when said cap is placed over a portion of the cervix, said ridged section having inner and outer surfaces; a recess formed in said ridged section by a pair of first and second substantially parallel walls and a third wall substantially perpendicular to said first and second walls; first and second helical shaped ridge portions defined by said recess along said inner surface; said first and second helical shaped ridge portions having a blunt inner edge, and adapted to remain substantially fixed and substantially parallel to form a substantiallly fluid-tight fit with said cervix while said cap is placed over a portion of the cervix, said cap being made of a flexible resilient material.

15. A cervical cap as recited in claim 14, wherein said dome-shaped portion is sealed.

16. A cervical cap as recited in claim 15, wherein the inside diameter of said ridged section progressively decreases toward said dome portion.

17. A cervical cap as recited in claim 16, wherein the inside diameter of said dome-shaped portion progressively increases toward said ridged section.

18. A cervical cap as recited in claim 17, wherein said ridged section is tapered such that the distance between said inner and outer surface at said ridged section progressively increases towards said open end portion.

19. A cervical cap as recited in claim 18, wherein said dome-shaped portion is of substantially uniform thickness.

* * * * *